United States Patent
Baghdadli et al.

(10) Patent No.: US 10,857,087 B2
(45) Date of Patent: *Dec. 8, 2020

(54) PROCESS FOR TREATING KERATIN FIBRES WITH A POLYSACCHARIDE AND A PYRIDINEDI-CARBOXYLIC ACID COMPOUND

(71) Applicant: L'OREAL, Paris (FR)

(72) Inventors: Nawel Baghdadli, Massy (FR); Isabelle Pasini, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/021,438

(22) PCT Filed: Sep. 11, 2014

(86) PCT No.: PCT/EP2014/069381
§ 371 (c)(1),
(2) Date: Mar. 11, 2016

(87) PCT Pub. No.: WO2015/036476
PCT Pub. Date: Mar. 19, 2015

(65) Prior Publication Data
US 2016/0228346 A1    Aug. 11, 2016

(30) Foreign Application Priority Data

Sep. 12, 2013 (FR) .................................. 13 58763

(51) Int. Cl.
| | | |
|---|---|---|
| *A61K 8/73* | (2006.01) |
| *A61K 8/49* | (2006.01) |
| *A61Q 5/12* | (2006.01) |
| *A61Q 5/00* | (2006.01) |
| *A45D 2/00* | (2006.01) |
| *A61Q 5/06* | (2006.01) |
| *A45D 7/06* | (2006.01) |

(52) U.S. Cl.
CPC .............. *A61K 8/73* (2013.01); *A61K 8/4926* (2013.01); *A61Q 5/12* (2013.01); *A45D 2/001* (2013.01); *A45D 7/06* (2013.01); *A61K 2800/882* (2013.01); *A61K 2800/884* (2013.01); *A61Q 5/002* (2013.01); *A61Q 5/06* (2013.01)

(58) Field of Classification Search
None
See application file for complete search history.

(56) References Cited

U.S. PATENT DOCUMENTS

| | | | |
|---|---|---|---|
| 3,724,092 A * | 4/1973 | McCleerey | A45D 20/44 34/90 |
| 4,185,087 A | 1/1980 | Morlino | |
| 4,452,261 A | 6/1984 | Bresak et al. | |
| 4,717,727 A | 1/1988 | Gunzler et al. | |
| 4,770,873 A | 9/1988 | Wolfram et al. | |
| 5,004,748 A | 4/1991 | Baader et al. | |
| 5,046,516 A | 9/1991 | Barradas | |
| 5,143,926 A | 9/1992 | Baader et al. | |
| 5,356,909 A | 10/1994 | Baader et al. | |
| 5,618,523 A | 4/1997 | Zysman et al. | |
| 5,665,778 A | 9/1997 | Semeria et al. | |
| 5,773,611 A | 6/1998 | Zysman et al. | |
| 5,957,140 A | 9/1999 | McGee | |
| 5,959,127 A | 9/1999 | Semeria et al. | |
| 5,992,425 A | 11/1999 | Teratani et al. | |
| 6,110,450 A | 8/2000 | Bergmann | |
| 8,163,273 B2 | 4/2012 | Devin-Baudoin et al. | |
| 2002/0172653 A1 | 11/2002 | Cannell et al. | |
| 2002/0187117 A1 | 12/2002 | Devin-Baudoin et al. | |
| 2002/0193264 A1 | 12/2002 | Cannell et al. | |
| 2003/0223945 A1 | 12/2003 | Dalko et al. | |
| 2005/0013786 A1 | 1/2005 | Sabbagh et al. | |
| 2005/0227902 A1 | 10/2005 | Erazo-Majewicz et al. | |
| 2008/0226576 A1 | 9/2008 | Benabdillah et al. | |
| 2009/0044823 A1 | 2/2009 | Overend et al. | |
| 2009/0215837 A1 | 8/2009 | Dalko et al. | |
| 2010/0016886 A1 | 1/2010 | Lu | |
| 2010/0105741 A1 | 4/2010 | Dalko et al. | |
| 2010/0263683 A1 | 10/2010 | Dutheil-Gouret et al. | |
| 2011/0020258 A1 | 1/2011 | Lorant | |
| 2011/0150812 A1 | 6/2011 | Mecca | |

(Continued)

FOREIGN PATENT DOCUMENTS

| | | |
|---|---|---|
| EP | 0095238 A2 | 11/1983 |
| EP | 0176741 A1 | 4/1986 |

(Continued)

OTHER PUBLICATIONS

English translation of FR 2944967; accessed Nov. 21, 2016.*
International Search Report for PCT/EP2014/069377, dated Jan. 22, 2015.
International Search Report for PCT/EP2014/069378, dated Jan. 21, 2015.
International Search Report for PCT/EP2014/069380, dated Jan. 22, 2015.
International Search Report for PCT/EP2014/069381, dated Feb. 13, 2015.

(Continued)

*Primary Examiner* — Nicole P Babson
(74) *Attorney, Agent, or Firm* — The Marbury Law Group, PLLC

(57) ABSTRACT

The invention relates to a process for treating keratin fibres, in particular human keratin fibres such as the hair, comprising: (i) a step of applying an oxidized polysaccharide, (ii) a step of heating to a temperature of at least 100° C., (iii) a step of applying a pyridinedicarboxylic acid compound. The process makes it possible to obtain good hair-conditioning cosmetic properties, with a long-lasting effect. The invention also relates to a cosmetic composition and a kit used for performing the treatment process.

13 Claims, No Drawings

(56) References Cited

U.S. PATENT DOCUMENTS

| | | |
|---|---|---|
| 2011/0268681 A1 | 11/2011 | Gonzalez et al. |
| 2013/0131095 A1 | 5/2013 | Dalko et al. |
| 2014/0076346 A1 | 3/2014 | Bourdin et al. |

FOREIGN PATENT DOCUMENTS

| | | |
|---|---|---|
| EP | 0217635 A2 | 4/1987 |
| EP | 0281943 A2 | 9/1988 |
| EP | 0500437 A1 | 8/1992 |
| EP | 0530974 A1 | 3/1993 |
| EP | 0647617 A1 | 4/1995 |
| EP | 1352629 A1 | 10/2003 |
| EP | 1468667 A1 | 10/2004 |
| FR | 2823110 A1 | 10/2002 |
| FR | 2838336 A1 | 10/2003 |
| FR | 2842200 A1 | 1/2004 |
| FR | 2854161 A1 | 10/2004 |
| FR | 2910275 A1 | 6/2008 |
| FR | 2932382 A1 | 12/2009 |
| FR | 2944438 A1 | 10/2010 |
| FR | 2944967 A1 | 11/2010 |
| FR | 2961394 A1 | 12/2011 |
| FR | 2975593 A1 | 11/2012 |
| WO | 2006/057437 A1 | 6/2006 |
| WO | 2007/090554 A1 | 8/2007 |
| WO | 2009/150198 A1 | 12/2009 |
| WO | 2010/070235 A2 | 6/2010 |
| WO | 2011/161020 A1 | 12/2011 |
| WO | 2013/132062 A1 | 9/2013 |
| WO | 2015/036473 A1 | 3/2015 |
| WO | 2015/036474 A1 | 3/2015 |
| WO | 2015/036475 A1 | 3/2015 |
| WO | 2015/036477 A1 | 3/2015 |

OTHER PUBLICATIONS

International Search Report for PCT/EP2014/069383, dated Feb. 11, 2015.
English language Abstract for FR 2944967A1 (Nov. 5, 2010).
English language Abstract for FR 2842200A1 (Jan. 16, 2004).
English language Abstract for FR 2854161A1 (Oct. 29, 2004).
Office Action for counterpart application CN201480050160.5 dated Apr. 24, 2017.
Office Action for counterpart application CN201480050160.5 dated Nov. 27, 2017.
Office Action for counterpart U.S. Appl. No. 15/021,452, dated Jul. 27, 2017.
Office Action for counterpart U.S. Appl. No. 15/021,402, dated Apr. 6, 2017.
Office Action for counterpart U.S. Appl. No. 15/021,042, dated Sep. 28, 2017.
Non-Final Office Action for copending U.S. Appl. No. 14/383,993, dated Jul. 30, 2015 (now U.S. Pat. No. 10,085,931).
Final Office Action for copending U.S. Appl. No. 14/383,993, dated Apr. 8, 2016 (now U.S. Pat. No. 10,085,931).
Non-Final Office Action for copending U.S. Appl. No. 14/383,993, dated Aug. 22, 2017 (now U.S. Pat. No. 10,085,931).
International Search Report for counterpart Application No. PCT/EP2013/054720, dated Apr. 22, 2013.
Final Office Action for copending U.S. Appl. No. 15/021,452, dated Mar. 22, 2018.
Non-Final Office Action for copending U.S. Appl. No. 15/021,402, dated Jan. 8, 2019.
Fryxell, Anna K., "Get Your Straightest Hair Ever With These Tools," <https://www.newbeauty.com/blog/dailybeauty/6572-final-get-your-straightest-hair-ever-with-these-tools/>, Aug. 31, 2012.
Non-Final Office Action for copending U.S. Appl. No. 15/021,452, dated Jan. 9, 2019.
Final Office Action for co-pending U.S. Appl. No. 15/021,452, dated Oct. 11, 2019.
Final Office Action for co-pending U.S. Appl. No. 15/021,402, dated October 10, 2019.
Non-Final Office Action for copending U.S. Appl. No. 16/331,378, dated Sep. 2, 2020.

* cited by examiner

PROCESS FOR TREATING KERATIN FIBRES WITH A POLYSACCHARIDE AND A PYRIDINEDI-CARBOXYLIC ACID COMPOUND

CROSS REFERENCE TO RELATED APPLICATIONS

This is a national stage application of PCT/EP2014/069381, filed internationally on Sep. 11, 2014, which claims priority to French Application No. 1358763, filed on Sep. 12, 2013, both of which are incorporated by reference herein in their entireties.

The invention relates to a cosmetic process for treating keratin fibres, in particular human keratin fibres such as the hair, using an oxidized polysaccharide and a pyridinedicarboxylic acid compound.

Hair is generally damaged and embrittled by the action of external atmospheric agents such as light, sunlight and bad weather, and also by mechanical or chemical treatments, such as brushing, combing, dyeing, bleaching, permanent-waving, relaxing and repeated washing. Hair is thus damaged by these various factors and may in the long run become dry, coarse, brittle or dull or split or limp.

Thus, to overcome these drawbacks, it is common practice to resort to hair treatments which make use of compositions intended for conditioning the hair appropriately by giving it satisfactory cosmetic properties, especially a soft feel (the hair is no longer coarse), good disentangling properties leading to easy combing, and good manageability of the hair which is thus easy to shape.

These haircare compositions may be, for example, conditioning shampoos, hair conditioners, masks or sera.

However, the conditioning effect obtained fades out in the course of successive shampoo washes and does not show satisfactory persistence on shampooing.

In the field of dyeing, patent application FR 2 944 967 discloses the use of oxidized polysaccharides for protecting the colour of keratin fibres that have been artificially dyed, especially by oxidation dyeing or direct dyeing.

There is thus a need for a process for treating keratin fibres, in particular the hair, that is capable of durably conditioning the keratin fibres, the conditioning effect being persistent after one or more shampoo washes performed on the treated keratin fibres.

The Applicant has discovered that the application to keratin fibres, in particular the hair, of an oxidized polysaccharide and a pyridinedicarboxylic acid derivative as defined below followed by a heating step makes it possible to obtain good hair-conditioning cosmetic properties, with a long-lasting effect, especially after shampooing one or more times.

Thus, one subject of the invention is a process for treating keratin fibres, in particular the hair, comprising:
(i) a step of applying to the keratin fibres at least one oxidized polysaccharide as defined below;
(ii) a step of heating the keratin fibres to a temperature of at least 100° C., preferably ranging from 100 to 250° C.;
(iii) a step of applying to the said fibres a pyridinedicarboxylic acid compound as defined below.

The treatment process according to the invention makes it possible to obtain good keratin fibre-conditioning cosmetic properties. In particular, the treatment process is a process for repairing damaged keratin fibres.

In particular, hair treated via the process according to the invention remains managed since no presence of frizziness is observed. Thus, the hairs are aligned, smooth and disentangle easily, which makes them easier to comb. The treated hair also has more body (it is not limp) and is thus easier to style. The treated hair shapes well.

Moreover, the treated hair is also shinier and feels softer. It is stronger and less brittle.

After treatment, the hair is not lank, and has a natural feel.

The process according to the invention has the advantage of giving good persistence of these hair-conditioning cosmetic properties after shampooing. Thus, the treated hair is durably conditioned.

A subject of the invention is also a cosmetic composition comprising, in a physiologically acceptable medium, a polysaccharide and a pyridinedicarboxylic acid compound as defined below.

A subject of the invention is also a kit comprising:
a first cosmetic composition comprising an oxidized polysaccharide as defined below and a second cosmetic composition comprising a pyridinedicarboxylic acid compound as defined below, the first and second compositions each being packaged in a separate packaging assembly.

A subject of the invention is also a kit comprising:
either a cosmetic composition comprising in an aqueous medium an oxidized polysaccharide and a pyridinedicarboxylic acid compound as defined below, the composition being contained in a packaging assembly,
or a first cosmetic composition comprising an oxidized polysaccharide as defined below and a second cosmetic composition comprising a pyridinedicarboxylic acid compound as defined below, the first and second compositions each being packaged in a separate packaging assembly,
and a device for heating the keratin fibres to a temperature of at least 100° C., preferably ranging from 100 to 250° C., such as those described below.

The composition packaging assembly is, in a known manner, any packaging that is suitable for storing cosmetic compositions (especially a bottle, tube, spray bottle or aerosol bottle).

Such a kit allows the keratin fibre treatment process according to the invention to be performed.

The oxidized polysaccharide(s) used in the process according to the invention are preferably anionic or nonionic polysaccharides.

The anionic or nonionic oxidized polysaccharides consist of monosaccharide units that may comprise five or more carbon atoms, preferably six or more carbon atoms, and more particularly six carbon atoms.

The nonionic or anionic oxidized polysaccharides comprise one or more aldehyde groups and optionally one or more anionic groups.

These anionic groups are preferably carboxylic or carboxylate groups.

The anionic or nonionic oxidized polysaccharides may be represented by formula (I) below:

$$P-(CHO)_m(COOX)_n \qquad (I)$$

in which:
P represents a polysaccharide chain consisting of monosaccharides comprising 5 carbon atoms or more than 5 carbon atoms, preferably 6 or more than 6 carbon atoms and more particularly 6 carbon atoms;
X is chosen from a hydrogen atom, the ions derived from an alkali metal or an alkaline-earth metal such as sodium or potassium, ammonia, organic amines such as monoethanolamine, diethanolamine, triethanolamine and 3-amino-1,2-propanediol and basic amino acids such as lysine, arginine, sarcosine, ornithine and citrulline,
m+n is greater than or equal to 1, m is such that the degree of substitution of the polysaccharide with one or more aldehyde groups (DS(CHO)) is within the range from 0.001 to 2 and preferably from 0.005 to 1.5, n is such that the degree of substitution of the polysaccharide with one or more carboxylic groups (DS(COOX)) is within the range from 0 to 2 and preferably from 0.001 to 1.5.

The term "degree of substitution DS(CHO) or DS(COOX) of the polysaccharides according to the invention" means the ratio between the number of carbons oxidized as an aldehyde or carboxylic group for all the repeating units and the number of elemental monosaccharides (even opened by preoxidation) constituting the polysaccharide.

The groups CHO and COOX may be obtained during the oxidation of certain carbon atoms, for example in position $C_2$, $C_3$ or $C_6$, of a saccharide unit comprising 6 carbon atoms. Preferably, the oxidation may take place at $C_2$ and at $C_3$, more particularly from 0.01% to 75% by number and preferably from 0.1% to 50% by number of the rings having possibly been opened.

The polysaccharide chain, represented by P, is preferably chosen from inulins, celluloses, starches, guar gums, xanthan gums, pullulan gums, alginate gums, agar-agar gums, carrageenan gums, gellan gums, gum arabics, xyloses and tragacanth gums, and derivatives thereof, cellobiose, maltodextrin, scleroglucan, chitosan, ulvan, fucoidan, alginate, pectin, heparin and hyaluronic acid, or mixtures thereof.

More preferentially, the polysaccharide chain is chosen from inulins and starches.

Even more preferentially, the polysaccharide chain is inulin.

The term "derivative" means the compounds obtained by chemical modification of the mentioned compounds. They may be esters, amides or ethers of the said compounds.

The oxidation may take place according to a process known in the art, for example according to the process described in FR 2 842 200, in document FR 2 854 161 or in the article "Hydrophobic films from maize bran hemicelluloses" by E. Fredon et al., Carbohydrate Polymers 49, 2002, pages 1 to 12. Another oxidation process is described in the article "water soluble oxidized starches by peroxide reaction extrusion" Industrial Crops and Products 75 (1997) 45-52—R. E. Wing, J. L. Willet. These oxidation processes are easy to perform, are efficient and do not generate any toxic by-products or by-products that are difficult to remove.

The peroxides that may be used in these oxidation processes may be an alkali metal or alkaline-earth metal percarbonate or perborate, an alkyl peroxide, peracetic acid or hydrogen peroxide. Hydrogen peroxide is particularly preferred, insofar as it is readily accessible and does not produce interfering by-products.

The amount of peroxide in the reaction medium is between 0.05 and 1 molar equivalent per glucose unit of the polysaccharide, preferably between 0.1 and 0.8 molar equivalent. It is preferable to add the peroxide in successive portions, leaving the reaction medium stirring between two additions.

A single phthalocyanin or a mixture of phthalocyanins, for example a mixture of cobalt phthalocyanin and of iron phthalocyanin, may be used as catalyst in the oxidation process. The amount of catalyst depends on the desired degree of substitution. In general, a small amount, for example an amount corresponding to 0.003 to 0.016 molar equivalent per 100 glucose units of polysaccharide, is suitable for use.

The process may also be performed by placing the polysaccharide in pulverulent form in contact with the catalyst dissolved in a small volume of water and with the peroxide. This process is referred to as a "semi-dry" process.

The process may be performed by reactive extrusion in the presence of peroxide.

More preferentially, the polysaccharide is obtained by oxidation of inulin, cellulose, carboxymethylcellulose, hydroxyethylcellulose, hydroxypropylcellulose, hydroxypropylmethylcellulose, methylcellulose, starch, starch acetate, hydroxyethyl starch, hydroxypropyl starch, guar gum, carboxymethyl guar gum, carboxymethylhydroxypropyl guar gum, hydroxyethyl guar gum, hydroxypropyl guar gum, xylose, xanthan gum or carrageenan gum, cellobiose, maltodextrin, scleroglucan, chitosan, ulvan, fucoidan, alginate, pectin, heparin and hyaluronic acid, or mixtures thereof.

Preferentially, the polysaccharide is obtained by oxidation of inulin or starch.

Preferentially, the polysaccharide is obtained by oxidation of inulin.

According to one embodiment, the polysaccharide is obtained by oxidation of inulin by performing a reactive extrusion process in the presence of hydrogen peroxide.

The polysaccharide chain before and after oxidation preferably has a weight-average molecular mass ranging from 400 to 15 000 000, better still from 500 to 10 000 000 and more particularly from 500 to 50 000 g/mol.

The polysaccharides that are most particularly preferred in the invention are those corresponding to formula (I) in which: P represents a polymer chain derived from inulin or from starch, m is such that the degree of substitution of the polysaccharide with one or more aldehyde groups (DS(CHO)) is within the range from 0.005 to 2.5, n is such that the degree of substitution of the polysaccharide with one or more carboxylic groups (DS(COOX)) is within the range from 0.001 to 2.

Even more preferably, P represents a polymer chain derived from inulin, m is such that the degree of substitution of the polysaccharide with one or more aldehyde groups (DS(CHO)) is within the range from 0.01 to 1, n is such that the degree of substitution of the polysaccharide with one or more carboxylic groups (DS(COOX)) is within the range from 0.01 to 2.

Advantageously, the step of applying the oxidized polysaccharide consists in applying a cosmetic composition comprising the oxidized polysaccharide especially in a content ranging from 0.05% to 15% by weight, preferably ranging from 0.1% to 10% by weight and more preferentially ranging from 0.2% to 6% by weight relative to the total weight of the composition.

The 2,4-pyridinedicarboxylic acid derivative used according to the invention is chosen from the compounds of formula (II) below:

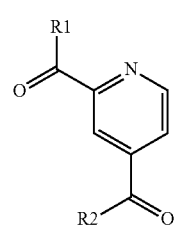

(II)

in which R1 and R2 represent, independently of each other, OH, OR', —NH2, —NHR', —NR'R", and R' and R" represent, independently of each other, a linear or branched, saturated or unsaturated C1-C18 alkyl, optionally substituted with at least one group chosen from OH, C1-C6 alkoxy, C1-C6 acyloxy, amino, (C1-C6)alkyloxycarbonyl or (C1-C6)alkylamino, or C6-C10 aryl,
or salts thereof.

More particularly, R1 and R2 represent, independently of each other, OH or OR', R' represent, independently of each other, a linear or branched, saturated C1-C12 alkyl, optionally substituted with at least one OH, C1-C4 alkoxy, C1-C4 acyloxy, (C1-C4)alkyloxycarbonyl or (C1-C4)alkylamino group, or phenyl.

In a particularly preferred manner, R1 and R2 represent, independently of each other, OH or OR', and R' represent, independently of each other, a linear or branched, saturated C1-C6 alkyl, optionally substituted with at least one OH, C1-C4 alkoxy, C1-C4 acyloxy, (C1-C4)alkyloxycarbonyl or (C1-C4)alkylamino group, or phenyl, or a salt of one of these compounds.

The following 2,4-pyridinedicarboxylic acid derivatives are preferred in the context of the present invention:
2,4-pyridinedicarboxylic acid (compound 2) or a salt thereof, especially the disodium salt (compound 1)
dimethyl 2,4-pyridinedicarboxylate (compound 3)
diethyl 2,4-pyridinedicarboxylate (compound 4)
2-ethyl ester of 2,4-pyridinedicarboxylic acid (compound 8)
4-ethyl ester of 2,4-pyridinedicarboxylic acid (compound 10)
diisopropyl 2,4-pyridinedicarboxylate (compound 6)
2,4-pyridinedicarboxylic acid di-n-propylamide
2-isopropyl ester of 2,4-pyridinedicarboxylic acid (compound 7)
methyl glycolate ester of 2,4-pyridinedicarboxylic acid Compound 1

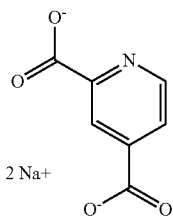

Compound 2

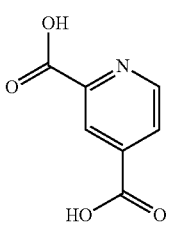

Compound 3

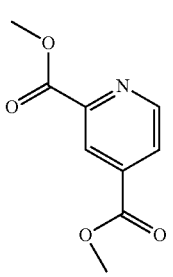

Compound 4

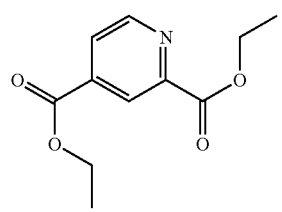

Compound 5

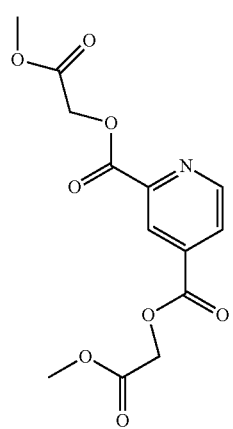

Compound 6

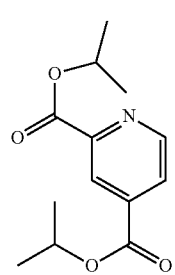

Compound 7

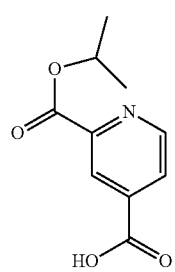

Compound 8

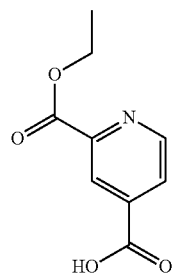

-continued

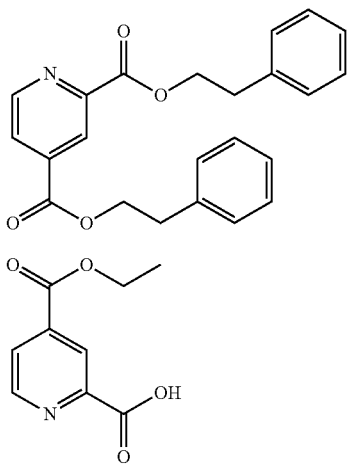

Compound 9

Compound 10

According to the invention, the term "salts of the compounds of formula (II)" means the organic or mineral salts of a compound of formula (I), these salts being physiologically acceptable. Mineral salts that may be mentioned include the sodium or potassium salts and also the salts of zinc ($Zn^{2+}$), of calcium ($Ca^{2+}$), of copper ($Cu^{2+}$), of iron ($Fe^{2+}$), of strontium ($Sr^{2+}$), of magnesium ($Mg^{2+}$), of manganese ($Mn^{2+}$); the hydroxides, the carbonates and the chlorides. Organic salts that may be mentioned include the triethanolamine, monoethanolamine, diethanolamine, hexadecylamine, N,N,N',N'-tetrakis(2-hydroxypropyl)ethylenediamine and tris(hydroxymethyl)aminomethane salts.

The compounds of formula (II) are known per se; they are especially described, along with their manufacture, in patent EP 1 352 629.

Advantageously, the step of applying the 2,4-pyridinedicarboxylic acid compound consists in applying a cosmetic composition comprising the said compound, especially in a content ranging from 0.1% to 10% by weight, preferably ranging from 0.5% to 8% by weight and more preferentially ranging from 0.5% to 6% by weight relative to the total weight of the composition.

The cosmetic composition(s) used according to the invention contain a physiologically acceptable medium, i.e. a medium that is compatible with human keratin materials such as the skin (of the body, face, around the eyes or the scalp), the hair, the eyelashes, the eyebrows, bodily hair, the nails or the lips.

The physiologically acceptable medium of the composition(s) used in the process according to the invention is advantageously an aqueous medium. It may consist, for example, of water or of a mixture of water and of at least one cosmetically acceptable organic solvent. Examples of organic solvents that may be mentioned include $C_2$-$C_4$ lower alcohols, such as ethanol and isopropanol; polyols, especially those containing from 2 to 6 carbon atoms, for instance glycerol, propylene glycol, butylene glycol, pentylene glycol, hexylene glycol, dipropylene glycol or diethylene glycol; polyol ethers, for instance 2-butoxyethanol, propylene glycol monomethyl ether and diethylene glycol monomethyl ether or monoethyl ether; and mixtures thereof.

Preferably, the cosmetic composition comprises from 50% to 99.5% by weight of water relative to the weight of the composition.

The composition used according to the invention may also contain one or more cosmetic additives chosen from nonionic, anionic, cationic and amphoteric surfactants, vitamins and provitamins, including panthenol, sunscreens, fillers, dyestuffs, nacreous agents, opacifiers, sequestrants, film-forming polymers, plasticizers, thickeners, oils, antioxidants, antifoams, moisturizers, emollients, penetrants, fragrances and preserving agents.

The composition used according to the invention may be in any galenical form conventionally used for application to the hair and in particular in the form of aqueous solutions, aqueous-alcoholic solutions, oil-in-water (O/W), water-in-oil (W/O) or multiple (triple: W/O/W or O/W/O), aqueous gels or aqueous-alcoholic gels. These compositions are prepared according to the usual methods. Preferably, the composition is in the form of an aqueous or aqueous-alcoholic solution or gel.

The process according to the invention comprises a step of heating the keratin fibres to a temperature of at least 100° C., preferably ranging from 100 to 250° C. Preferably, the step of heating the keratin fibres is performed at a temperature ranging from 150 to 220° C., preferably ranging from 160° C. to 220° C., preferentially ranging from 160° C. to 200° C. and especially ranging from 170° C. to 190° C.

This heating step is advantageously performed using an iron.

The heating step makes it possible to optimize the effects of the process, and especially to optimize the persistence of the cosmetic properties after shampooing one or more times.

For the purposes of the present invention, the term "iron" means a device for heating keratin fibres by placing the said fibres and the heating device in contact. The end of the iron which comes into contact with the keratin fibres generally has two flat surfaces. These two surfaces may be made of metal or ceramic. In particular, these two surfaces may be smooth or crimped or curved.

The heating step may be performed by means of a straightening iron, a curling iron, a crimping iron or a steam iron. Preferably, the heating step is performed using a straightening iron.

As examples of irons that may be used in the straightening process according to the invention, mention may be made of any type of flat iron, and in particular, in a nonlimiting manner, those described in patents U.S. Pat. Nos. 5,957,140 and 5,046,516.

The iron may be applied by successive separate strokes lasting a few seconds or by gradual movement or sliding along the locks of keratin fibres, especially of hair.

Preferably, the iron is applied in the process according to the invention by a continuous movement from the root to the end, in one or more passes, in particular in two to twenty passes. The duration of each pass of the iron may last from 2 seconds to 1 minute.

Preferably, the step of heating the keratin fibres is performed for a time that may range from 2 seconds to 30 minutes, preferentially from 2 seconds to 20 minutes, better still from 2 seconds to 10 minutes, better still from 2 seconds to 5 minutes and even better still from 2 seconds to 2 minutes.

The process according to the invention may also comprise an additional step of drying the keratin fibres after the application of the oxidized polysaccharide and/or of the pyridinedicarboxylic acid compound or of the cosmetic composition(s) containing the same and before the step of heating the keratin fibres performed at a temperature of at least 100° C. The drying step may be performed using a hairdryer or a hood or by open drying. The drying step is advantageously performed at a temperature ranging from 20 to 70° C.

After the drying step, the keratin fibres may be optionally rinsed with water or washed with a shampoo. The keratin fibres are then optionally dried using a hairdryer or a hood or in the open air.

According to one embodiment, the process according to the invention is performed on natural keratin fibres, especially natural hair.

According to another embodiment, the process according to the invention is performed on damaged keratin fibres, especially damaged hair. As indicated previously, the term "damaged hair" means dry or coarse or brittle or split or limp hair.

According to another embodiment, the treatment process according to the invention is preferably performed on sensitized keratin fibres, especially sensitized hair, such as bleached, artificially dyed, relaxed or permanent-waved fibres.

The process according to the invention may be performed on keratin fibres, especially hair, which are dry or wet. Preferentially, the process is performed on dry keratin fibres, especially dry hair.

The cosmetic composition(s) used according to the invention are advantageously applied to the keratin fibres in an amount ranging from 0.1 to 10 grams and preferably from 0.2 to 5 grams of composition per gram of keratin fibres. After application of the cosmetic composition to the keratin fibres, they may be manually dried to remove the excess composition or washed with water or with a shampoo.

After application to the keratin fibres of the oxidized polysaccharide and/or of the pyridinedicarboxylic acid compound, or of a cosmetic composition containing the same, and before performing the step of heating the keratin fibres, the oxidized polysaccharide and/or the pyridinedicarboxylic acid compound or the composition(s) containing the same may be applied for a time ranging from 1 to 60 minutes, preferably ranging from 2 to 50 minutes and preferentially ranging from 5 to 45 minutes. The composition may be left on at a temperature ranging from 15° C. to 45° C., preferably at room temperature (25° C.).

According to one embodiment of the process according to the invention, the oxidized polysaccharide and the pyridinedicarboxylic acid compound are present in separate cosmetic compositions. They are therefore applied separately to the keratin fibres.

According to another embodiment of the process according to the invention, the oxidized polysaccharide and the pyridinedicarboxylic acid compound are present in the same cosmetic composition. They are therefore applied simultaneously to the keratin fibres.

According to a first embodiment of the process according to the invention, the following steps are performed, in the following order: the step of applying the oxidized polysaccharide, then the step of applying the pyridinedicarboxylic acid compound and then the heating step. Advantageously, the polysaccharide is present in a first cosmetic composition and the pyridinedicarboxylic acid compound is present in a second cosmetic composition. This second composition is separate from the first composition.

According to a second embodiment of the process according to the invention, the following steps are performed, in the following order: simultaneously, the step of applying the oxidized polysaccharide and the step of applying the pyridinedicarboxylic acid compound and then the heating step. Advantageously, the oxidized polysaccharide and the pyridinedicarboxylic acid compound are present in a single cosmetic composition.

According to a third embodiment of the process according to the invention, the following steps are performed, in the following order: the step of applying the oxidized polysaccharide, then the heating step, then the step of applying the pyridinedicarboxylic acid compound and then optionally an additional heating step.

The treatment process according to the invention may be performed before, during and/or after an additional process of cosmetic treatment of the keratin fibres, such as a process for temporarily shaping (shaping with curlers, a crimping iron or a straightening iron) or a process for durably shaping (permanent-waving or relaxing) the keratin fibres.

The treatment process may be performed as a pre-treatment to a dyeing or relaxing process and/or a permanent-waving process so as to cosmetically protect the keratin fibres against these treatments. In other words, this process is performed to preserve the cosmetic properties of the keratin fibres before a cosmetic treatment process as described previously.

In particular, the treatment process is performed as a post-treatment to a bleaching, artificial dyeing or relaxing process and/or a permanent-waving process so as to repair the said fibres.

The process according to the invention may be performed during a cosmetic treatment process so as to repair the said fibres.

In particular, the treatment process according to the invention may be performed on damaged keratin fibres.

In other words, the treatment process according to the invention is preferably performed on sensitized keratin fibres such as bleached, dyed, relaxed or permanent-waved fibres.

In particular, the treatment process may be performed before a bleaching, dyeing or relaxing process and/or a permanent-waving process on keratin fibres.

As a variant, the treatment process may be performed during and/or after a cosmetic process for treating keratin fibres, in particular:

(a) during and/or after a process of dyeing or a process of permanent-waving or a process of relaxing keratin fibres, and (b) after a process of bleaching keratin fibres.

According to one embodiment, the treatment process according to the invention is performed after a process of bleaching the keratin fibres.

The examples that follow are given as illustrations of the present invention. The amounts indicated in the examples are expressed as weight percentages.

Oxidized Polysaccharide Tested (Polymer 1)

Polymer 1 was prepared by oxidation of inulin sold under the name Inutec N25 by the company Orafti, by performing a reactive extrusion process as described in the article "Water-soluble oxidized starches by peroxide reactive extrusion" by R. E. Wing and J. L. Willett, Industrial Crops and Products 7, 1997, pages 45-52. A BC21 co-rotating twin-screw extruder sold by the company Clextral was used, and aqueous hydrogen peroxide solution was used as oxidizing agent.

Polymer 1: oxidized inulin obtained by reactive extrusion of a mixture of 78% by weight of inulin and 1.57% by weight of aqueous hydrogen peroxide solution; the spontaneous pH after reactive extrusion is 3.8. Compound 1 thus obtained has a carbonyl content of 1.23% (w/w) and a carboxyl content of 0.17% (w/w).

Compositions Prepared

| Compositions | B | C | D | X | Y |
|---|---|---|---|---|---|
| Polymer 1 | 1 | 1 | | | |
| diethyl 2,4-pyridinedicarboxylate | 5 | | 5 | | |
| Water/ethanol (50/50 weight/weight) | qs 100 | | qs 100 | | qs 100 |
| Water | | qs 100 | | qs 100 | |

Locks of type II natural frizzy hair were used.

Composition B (containing 1% of polymer 1 and 5% of diethyl 2,4-pyridinedicarboxylate) was applied to locks of hair and left on for 15 minutes at 40° C.

The locks were dried manually and then dried under a hood for 15 minutes at 60° C.

The locks were combed before applying a straightening iron at a temperature of 180° C. by performing five continuous passes through the locks for 5 seconds.

For comparative purposes, the same protocol was also performed on the locks with, independently, the placebo composition X, composition Y containing only water (control lock), composition C (containing 1% of polymer 1) and composition D (containing 5% of diethyl 2,4-pyridinedicarboxylate).

To evaluate the durable (persistent) nature of the cosmetic properties of the locks of hair, they were then washed with a shampoo according to the protocol described previously.

The cosmetic properties of the locks after shampooing were then evaluated, especially the cosmetic feel, the manageability and the ease of combing of the locks, the body effect and the sheen of the hair.

The following results were obtained:

| Type of lock of hair | Cosmetic properties after shampooing |
|---|---|
| Type II natural hair treated with composition (Y) (control) + iron (Lock 1) | Coarse feel; dry, dull, unmanageable lock, difficult to comb, hair lacking body |
| Type II natural hair treated with placebo composition (X) + iron (Lock 2) | Coarser feel; dull lock, difficult to comb, more manageable, no body effect |
| Type II natural hair treated with composition (C) + iron (Lock 3) | Softer feeling, shinier, more manageable lock, easier to comb, improved gloss. Better shaping |
| Type II natural hair treated with composition (D) + iron (Lock 4) | Even softer feeling hair (especially at the ends), more manageable, easier to comb. The hair has body and shapes better (better curl definition). Improved sheen. |
| Type II natural hair treated with composition (B) + iron (Lock 5) | Softest feeling, most manageable lock, easiest to comb. The hair has the most body and shapes better (better curl definition). Markedly improved sheen. |

The locks of hair were then classified as a function of their cosmetic properties (soft, pleasant cosmetic feel, manageability, ease of combing, sheen, body effect) after having been shampooed.

| After shampooing | Lock 5 > Lock 4 > Lock 3 > Lock 1 > Lock 2 |
|---|---|

Lock 5 treated via the process according to the invention, and after having been shampooed, has better cosmetic properties in terms of soft feel, manageability, ease of combing, sheen and body of the hair. These cosmetic properties thus have good persistence on shampooing.

In addition, the colour of the treated hair is not modified.

The same treatment as that described previously was performed, but using locks of sensitized type II frizzy hair (bleaching SA 20%).

The following results were obtained:

| Type of lock of hair | Cosmetic properties after shampooing |
|---|---|
| Sensitized type II hair treated with composition (Y) (control) + iron (Lock 1') | Coarse feel; dry, dull, unmanageable lock, difficult to comb, hair lacking body |
| Sensitized type II hair treated with placebo composition (X) + iron (Lock 2') | Coarser feel; dull lock, difficult to comb, more manageable, no body effect |
| Sensitized type II hair treated with composition (C) + iron (Lock 3') | Softer feeling, shinier, more manageable lock, easier to comb, improved gloss. Better shaping |
| Sensitized type II hair treated with composition (D) + iron (Lock 4') | Even softer feeling hair (especially at the ends), more manageable, easier to comb. The hair has body and shapes better (better curl definition). Improved sheen. |
| Sensitized type II hair treated with composition (B) + iron (Lock 5') | Softest feeling, most manageable lock, easiest to comb. The hair has the most body and shapes better (better curl definition). Markedly improved sheen. |

The locks of hair were then classified as a function of their cosmetic properties (soft, pleasant cosmetic feel, manageability, ease of combing, sheen, body effect) after having been shampooed.

| After shampooing | Lock 5' > Lock 4' > Lock 3' > Lock 1' > Lock 2' |
|---|---|

Lock 5 treated via the process according to the invention, and after having been shampooed, has better cosmetic properties in terms of soft feel, manageability, ease of combing, sheen and body of the hair. These cosmetic properties thus have good persistence on shampooing.

In addition, the colour of the treated hair is not modified.

The invention claimed is:

1. A process for protecting or conditioning keratin fibers, the process comprising:
   (i) applying to the keratin fibers at least one oxidized polysaccharide, wherein the at least one oxidized polysaccharide is chosen from those of formula (I):

P—(CHO)$m$(COOX)$n$     (I)

wherein:
   P represents a polysaccharide chain chosen from celluloses, hydroxyethylcelluloses, hydroxypropylcelluloses, carboxymethylcelluloses, starches, guar gums, inulins, xanthan gums, pullulan gums, agar-agar gums, carrageenan gums, gellan gums, gum arabics, tragacanth gums, xylans and derivatives thereof, cellobiose, maltodextrin, scleroglucan, chitosan, ulvan, fucoidan, alginate, pectin, heparin, or hyaluronic acid,
   X is chosen from a hydrogen atom, ions derived from an alkali metal or an alkaline-earth metal, sodium ion, potassium ion, ammonia, organic amines, monoethanolamine, diethanolamine, triethanolamine, 3-amino-1,2-propanediol, basic amino acids, lysine, arginine, sarcosine, ornithine, or citrulline, m+n is greater than or equal to 1,
   m is such that the degree of substitution of the polysaccharide with at least one aldehyde group (DS(CHO)) ranges from about 0.001 to about 2, and
   n is such that the degree of substitution of the polysaccharide with at least one carboxylic group (DS(COOX)) ranges from about 0 to about 2,
   wherein applying the oxidized polysaccharide comprises applying a cosmetic composition comprising the oxidized polysaccharide in an amount ranging from about 0.2% to about 6% by weight, relative to the total weight of the cosmetic composition,
(ii) heating the keratin fibers with an iron at a temperature of at least about 170° C., and
(iii) applying to the keratin fibers a pyridinedicarboxylic acid compound of formula (II) or salts thereof:

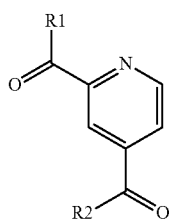
(II)

wherein:
   R1 and R2, independently, are chosen from OH, OR', —NH2, —NHR', or —NR'R",
   wherein R' and R", independently, are chosen from a linear or branched, saturated or unsaturated C1-C18 alkyl, optionally substituted with at least one group chosen from OH, C1-C6 alkoxy, C1-C6 acyloxy, amino, (C1-C6)alkyloxycarbonyl, (C1-C6)alkylamino, or C6-C10 aryl,
   wherein applying the pyridinedicarboxylic acid compound of formula (II) comprises applying a cosmetic composition comprising compound (II) in an amount ranging from about 0.5% to 6% by weight, relative to the total weight of the cosmetic composition.

2. The process according to claim 1, wherein the at least one oxidized polysaccharide is anionic or nonionic.

3. The process according to claim 1, wherein in the pyridinedicarboxylic acid compound of formula (II), R1 and R2, independently, are chosen from OH or OR'.

4. The process according to claim 1, wherein in the pyridinedicarboxylic acid compound of formula (II), R', independently, is chosen from a linear or branched, saturated C1-C12 alkyl or C1-C6 alkyl, optionally substituted with at least one OH, C1-C4 alkoxy, C1-C4 acyloxy, (C1-C4)alkyloxycarbonyl, (C1-C4)alkylamino, or phenyl.

5. The process according to claim 1, wherein the pyridinedicarboxylic acid compound of formula (II) is chosen from:

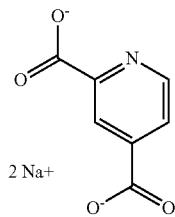

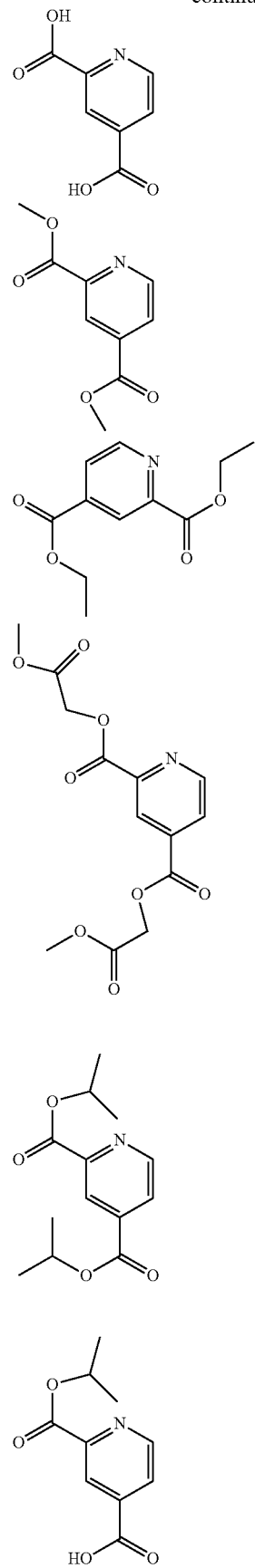

-continued

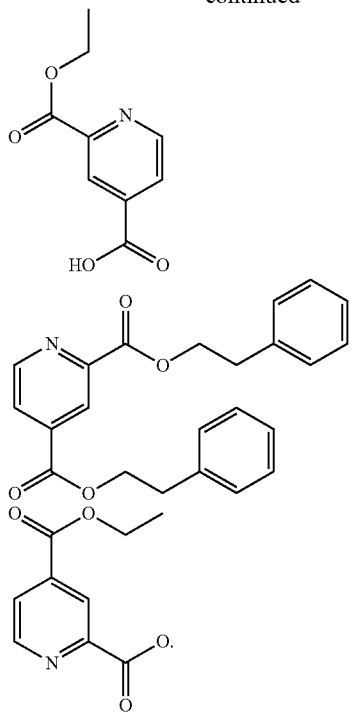

6. The process according to claim 1, wherein the heating step is performed at a temperature ranging from about 170° C. to about 250° C.

7. The process according to claim 1, wherein the steps are performed, in a sequence chosen from the following:

applying the at least one oxidized polysaccharide or a first cosmetic composition comprising the at least one oxidized polysaccharide, then applying the pyridinedicarboxylic acid compound of formula (II) or a second cosmetic composition comprising the pyridinedicarboxylic acid compound of formula (II), and then heating the keratin fibers;

applying the at least one oxidized polysaccharide or a first cosmetic composition comprising the at least one oxidized polysaccharide, and applying the pyridinedicarboxylic acid compound of formula (II) or a cosmetic composition comprising the pyridinedicarboxylic acid compound of formula (II), and then heating the keratin fibers;

applying the at least one oxidized polysaccharide or a first cosmetic composition comprising the at least one oxidized polysaccharide, then heating the keratin fibers, applying the pyridinedicarboxylic acid compound of formula (II) or a second cosmetic composition comprising the pyridinedicarboxylic acid compound of formula (II), and then optionally heating the keratin fibers an additional time.

8. The process according to claim 1, wherein the process further comprises drying the keratin fibers after the application of the at least one oxidized polysaccharide and/or of a first cosmetic composition comprising the same and/or of the pyridinedicarboxylic acid compound of formula (II) or of a second cosmetic composition comprising the same, and before heating the keratin fibers, the drying step being performed at a temperature ranging from about 20° C. to about 70° C.

9. The process according to claim 1, wherein after application to the keratin fibers of the at least one oxidized polysaccharide and/or of the pyridinedicarboxylic acid compound of formula (II), and before heating the keratin fibers, the at least one oxidized polysaccharide and/or the pyridinedicarboxylic acid compound of formula (II) is left on the keratin fibers for a time ranging from about 1 to about 60 minutes.

10. The process according to claim 1, wherein the heating step is performed with a straightening iron.

11. The process according to claim 1, wherein the heating step is performed by applying a straightening iron to the keratin fibers in a substantially continuous movement from the root to the end of the keratin fibers, in at least one pass.

12. The process according to claim 1, wherein the process is performed on damaged keratin fibers and/or hair.

13. The process according to claim 1, wherein either or both of the at least one oxidized polysaccharide and/or the pyridinedicarboxylic acid compound of formula (II) is present in a cosmetic composition comprising a physiologically acceptable aqueous medium.

* * * * *